US012670214B2

(12) United States Patent
 Macpherson

(10) Patent No.: US 12,670,214 B2
(45) Date of Patent: *Jun. 30, 2026

(54) DETERMINING FAMILY CONNECTIONS OF INDIVIDUALS IN A DATABASE

(71) Applicant: 23andMe, Inc., Sunnyvale, CA (US)

(72) Inventor: John Michael Macpherson, Santa Ana, CA (US)

(73) Assignee: 23andMe Genomics LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/961,840

(22) Filed: Nov. 27, 2024

(65) Prior Publication Data

US 2025/0094495 A1 Mar. 20, 2025

Related U.S. Application Data

(63) Continuation of application No. 18/315,237, filed on May 10, 2023, now abandoned, which is a continuation of application No. 17/488,184, filed on Sep. 28, 2021, now abandoned, which is a continuation of application No. 16/020,864, filed on Jun. 27, 2018, now Pat. No. 11,170,047, which is a continuation of application No. 13/910,890, filed on Jun. 5, 2013, now Pat. No. 10,025,877.

(60) Provisional application No. 61/656,298, filed on Jun. 6, 2012.

(51) Int. Cl.
 *G06F 7/00* (2006.01)
 *G06F 16/901* (2019.01)
 *G16B 10/00* (2019.01)
 *G16B 99/00* (2019.01)
 *G16H 10/60* (2018.01)
 *G16Z 99/00* (2019.01)

(52) U.S. Cl.
 CPC ......... *G06F 16/9024* (2019.01); *G16B 10/00* (2019.02); *G16B 99/00* (2019.02); *G16H 10/60* (2018.01); *G16Z 99/00* (2019.02)

(58) Field of Classification Search
 CPC ..... G06F 16/9024; G16B 10/00; G16B 99/00; G16H 10/60; G16Z 99/00
 See application file for complete search history.

(56) References Cited

U.S. PATENT DOCUMENTS

| | | | |
|---|---|---|---|
| 6,416,325 B2 * | 7/2002 | Gross ..................... | G09B 19/00 |
| | | | 434/154 |
| 6,760,731 B2 * | 7/2004 | Huff ...................... | G06F 16/958 |
| 6,941,317 B1 * | 9/2005 | Chamberlin ........... | G16B 50/30 |
| | | | 435/6.12 |
| 7,512,612 B1 * | 3/2009 | Akella .................... | H04L 51/52 |
| 7,660,815 B1 * | 2/2010 | Scofield .............. | G06F 16/9538 |
| | | | 707/999.102 |

(Continued)

*Primary Examiner* — Mohammed R Uddin
(74) *Attorney, Agent, or Firm* — McDonnell Boehnen Hulbert & Berghoff LLP

(57) ABSTRACT

Determining relative connections between individuals includes: obtaining identification information of a first individual and identification information of a second individual; determining, based at least in part on a relative connections graph, a relative connections path connecting the first individual, the second individual, and at least one additional individual; and outputting information pertaining to the relative connections path.

20 Claims, 11 Drawing Sheets

Last name: Robbins

Resident State: CA [Find People]

○ Sara Robbins

● Alice Robbins

○ Ted Robbins

[Find Shortest Path]

(56) References Cited

U.S. PATENT DOCUMENTS

| | | | | |
|---|---|---|---|---|
| 8,271,201 B2* | 9/2012 | Chakraborty | .......... | G16B 20/00 |
| | | | | 702/19 |
| 8,786,603 B2* | 7/2014 | Rasmussen | .......... | G06F 3/0485 |
| | | | | 715/855 |
| 8,913,797 B1* | 12/2014 | Siddavanahalli | ...... | G06V 20/30 |
| | | | | 382/118 |
| 11,936,648 B2* | 3/2024 | Buscemi | ............ | H04L 63/0861 |
| 2001/0034023 A1* | 10/2001 | Stanton, Jr. | ........... | G16B 20/20 |
| | | | | 435/6.16 |
| 2002/0032687 A1* | 3/2002 | Huff | .................... | G06F 16/958 |
| 2003/0172065 A1* | 9/2003 | Sorenson | .............. | G16B 10/00 |
| 2004/0229231 A1* | 11/2004 | Frudakis | ............. | C12Q 1/6876 |
| | | | | 435/6.14 |
| 2005/0075917 A1* | 4/2005 | Flores | .................... | G06Q 10/06 |
| | | | | 705/7.11 |
| 2005/0114364 A1* | 5/2005 | Tebbs | ..................... | G06Q 99/00 |
| 2005/0147947 A1* | 7/2005 | Cookson, Jr. | .......... | G06F 16/20 |
| | | | | 434/154 |
| 2006/0005118 A1* | 1/2006 | Golze | .................... | G06F 16/904 |
| | | | | 715/205 |
| 2006/0025929 A1* | 2/2006 | Eglington | .............. | G16B 20/00 |
| | | | | 702/19 |
| 2006/0036662 A1* | 2/2006 | Cornell | ................. | G06F 16/972 |
| 2006/0047725 A1* | 3/2006 | Bramson | ............ | G06F 21/6272 |
| 2006/0224631 A1* | 10/2006 | Kwon | .................... | G06Q 99/00 |
| 2006/0241869 A1* | 10/2006 | Schadt | .................. | G16B 20/00 |
| | | | | 702/19 |
| 2006/0287842 A1* | 12/2006 | Kim | .................. | G01N 29/0609 |
| | | | | 702/183 |
| 2006/0287876 A1* | 12/2006 | Jedlicka | ................. | G06Q 10/10 |
| | | | | 345/441 |
| 2007/0065017 A1* | 3/2007 | Kotwaliwale | ........ | G06V 30/422 |
| | | | | 382/226 |
| 2007/0168368 A1* | 7/2007 | Stone | .................... | G06Q 99/00 |
| 2007/0178500 A1* | 8/2007 | Martin | .................. | G16B 40/30 |
| | | | | 435/6.17 |
| 2007/0226248 A1* | 9/2007 | Darr | ...................... | H04L 67/535 |
| | | | | 707/999.102 |
| 2008/0040046 A1* | 2/2008 | Chakraborty | .......... | G16B 20/40 |
| | | | | 702/20 |
| 2008/0081331 A1* | 4/2008 | Myres | .................... | G16B 20/00 |
| | | | | 702/20 |
| 2008/0108027 A1* | 5/2008 | Sallin | ................. | G09B 19/0046 |
| | | | | 434/154 |
| 2008/0131887 A1* | 6/2008 | Stephan | .................. | G16B 20/20 |
| | | | | 707/999.01 |
| 2008/0154566 A1* | 6/2008 | Myres | .................... | G16B 45/00 |
| | | | | 703/11 |
| 2008/0172407 A1* | 7/2008 | Sacks | .................... | G06Q 10/10 |
| | | | | 707/999.102 |
| 2008/0215301 A1* | 9/2008 | Eyal | ........................ | G16B 15/20 |
| | | | | 703/11 |
| 2008/0227063 A1* | 9/2008 | Kenedy | .................. | G09B 19/00 |
| | | | | 434/219 |
| 2008/0270331 A1* | 10/2008 | Taylor | .................... | G06N 3/126 |
| | | | | 706/13 |
| 2008/0288886 A1* | 11/2008 | Sherwood | .......... | G06F 16/9024 |
| | | | | 715/772 |
| 2009/0118131 A1* | 5/2009 | Avey | ...................... | G16B 20/40 |
| | | | | 506/7 |
| 2009/0119083 A1* | 5/2009 | Avey | ...................... | G16B 20/40 |
| | | | | 703/11 |
| 2009/0240722 A1* | 9/2009 | Yu | ........................... | G06Q 10/10 |
| | | | | 707/999.102 |
| 2010/0049538 A1* | 2/2010 | Frazer | ............... | G06Q 30/0244 |
| | | | | 705/14.43 |
| 2010/0049736 A1* | 2/2010 | Rolls | .................... | G06F 16/212 |
| | | | | 707/E17.055 |
| 2010/0138374 A1* | 6/2010 | Chakraborty | .......... | G16B 20/00 |
| | | | | 706/46 |
| 2010/0223281 A1* | 9/2010 | Hon | ........................ | G16B 45/00 |
| | | | | 707/769 |
| 2011/0004581 A1* | 1/2011 | Schmidt | .................. | G06F 17/11 |
| | | | | 707/769 |
| 2011/0060844 A1* | 3/2011 | Allan | ...................... | H04L 45/00 |
| | | | | 709/241 |
| 2011/0137944 A1* | 6/2011 | Rolls | ...................... | G16H 10/60 |
| | | | | 707/E17.014 |
| 2011/0196924 A1* | 8/2011 | Hargarten | .............. | G06Q 30/02 |
| | | | | 709/204 |
| 2011/0202846 A1* | 8/2011 | Najork | .............. | G01C 21/3446 |
| | | | | 709/224 |
| 2012/0054190 A1* | 3/2012 | Peters | ...................... | G06T 3/40 |
| | | | | 707/812 |
| 2012/0140636 A1* | 6/2012 | Resende | ................ | H04L 45/08 |
| | | | | 370/238 |
| 2012/0207690 A1* | 8/2012 | Weill | ...................... | G06F 16/24 |
| | | | | 702/19 |
| 2012/0232796 A1* | 9/2012 | Keerthi | .............. | G01C 21/3476 |
| | | | | 701/400 |
| 2012/0331008 A1* | 12/2012 | Parida | ................ | G06F 16/9024 |
| | | | | 707/E17.011 |
| 2013/0131994 A1* | 5/2013 | Birdwell | ................ | G16B 40/00 |
| | | | | 702/19 |
| 2013/0155068 A1* | 6/2013 | Bier | ...................... | G06Q 10/06 |
| | | | | 345/440 |
| 2013/0254213 A1* | 9/2013 | Cheng | ................... | G06Q 50/01 |
| | | | | 707/E17.03 |
| 2013/0339352 A1* | 12/2013 | Jin | ...................... | G06F 16/9024 |
| | | | | 707/736 |
| 2014/0025308 A1* | 1/2014 | Jorde | .................... | G16B 20/40 |
| | | | | 702/19 |
| 2014/0278138 A1* | 9/2014 | Barber | .................. | G06F 16/252 |
| | | | | 702/19 |
| 2025/0277268 A1* | 9/2025 | Kim | ..................... | C12Q 1/6827 |

* cited by examiner

302

Last name:     Robbins

Resident State:     CA          Find People

○ Sara Robbins

● Alice Robbins

○ Ted Robbins          Find Shortest Path

Obtain identification information of a first individual and identification information of a second individual — 502

Determine, based at least in part on a genetic connections graph, a relative connections path connecting the first individual, the second individual, and at least one additional individual — 504

Output information pertaining to the determined path — 506

700

DETERMINING FAMILY CONNECTIONS OF INDIVIDUALS IN A DATABASE

CROSS-REFERENCE TO RELATED APPLICATIONS

The present application is a continuation application claiming priority to Non-Provisional patent application Ser. No. 18/315,237, filed May 10, 2023; which claims priority to Non-Provisional patent application Ser. No. 17/488,184, filed Sep. 28, 2021; which claims priority to Non-Provisional patent application Ser. No. 16/020,864, filed Jun. 27, 2018 and issued as U.S. Pat. No. 11,170,047 on Nov. 9, 2021; which claims priority to Non-Provisional patent application Ser. No. 13/910,890, filed Jun. 5, 2013 and issued as U.S. Pat. No. 10,025,877 on Jul. 17, 2018; which claims the benefit of Provisional Patent Application No. 61/656,298, filed Jun. 6, 2012. The contents of U.S. Pat. Nos. 11,170,047 and 10,025,877; Non-Provisional patents application Ser. No. 18/315,237, Ser. No. 17/488,184, Ser. No. 16/020,864, and Ser. No. 13/910,890; and Provisional Patent Application No. 61/656,298 are hereby incorporated by reference in their entireties.

BACKGROUND OF THE INVENTION

23andMe®, a personal genomics services company, has built up a large database comprising personal information (e.g., family information, genetic information, etc.) of hundreds of thousand users. One application provided by the company is Relative Finder, which uses genetic information to help users find genetic relatives (i.e., people who share a common ancestor) in the database. Within the large database, an individual may have many relatives, and there can be many ways the individual may be connected to a particular relative. Once the relatives of an individual are identified, it is often as important for the individual to understand how the connections are formed. Additional services are needed to provide insight into the family connections of individuals.

BRIEF DESCRIPTION OF THE DRA WINGS

Various embodiments of the invention are disclosed in the following detailed description and the accompanying drawings.

FIG. 4 is an example user interface used to invoke the pathfinding application.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Determining family connections (also referred to as relative connections) between two individuals is described. In some embodiments, a relative connections graph is formed for individuals whose genetic and/or family data is stored in a database. The relative connections graph indicates the relative relationships of these individuals. Based on the relative connections graph, a relative connections path connecting two individuals is determined. In some embodiments, the relative connections path is a shortest path.

Figure 1:
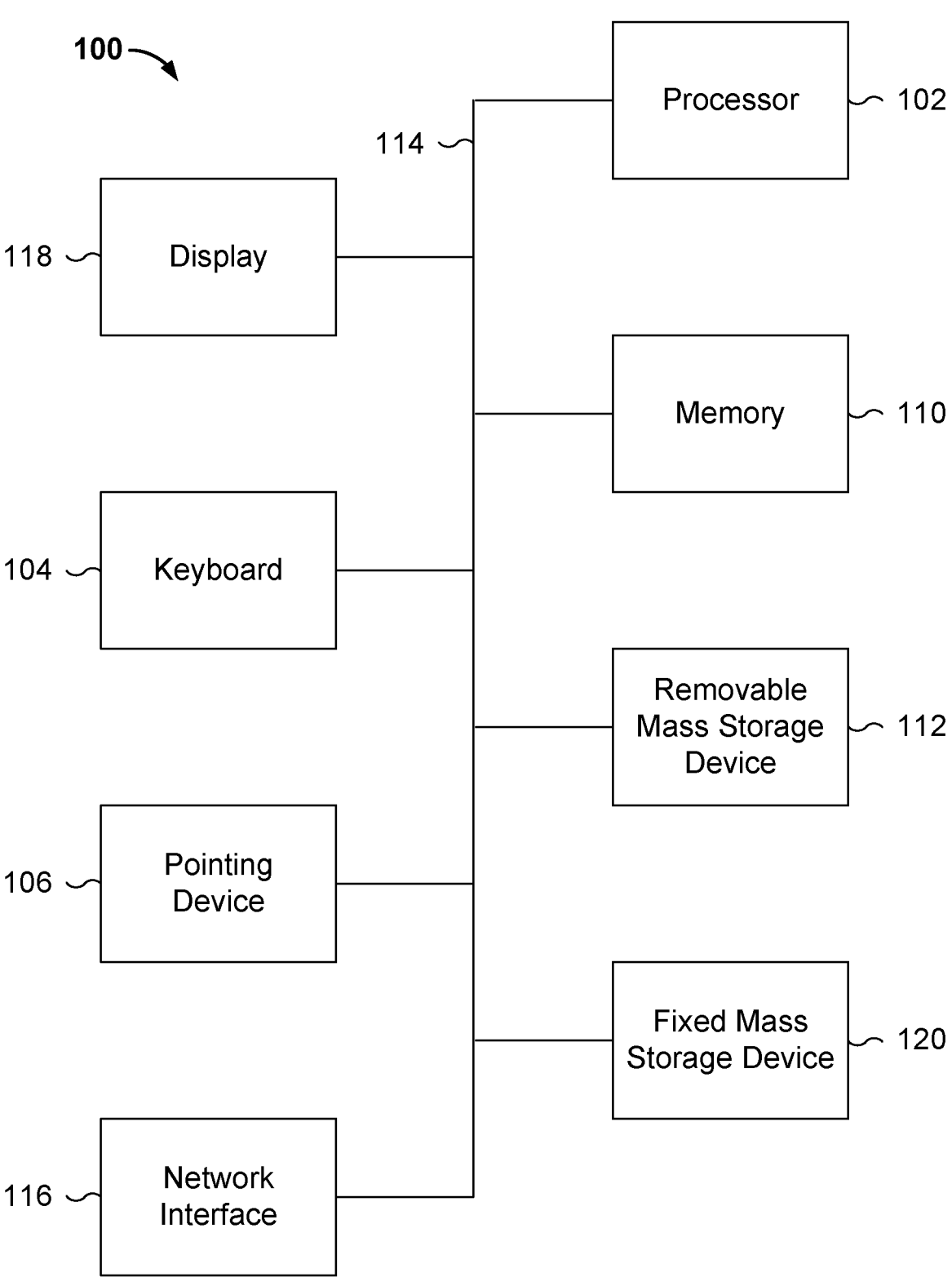
FIG. 1 is a functional diagram illustrating a programmed computer system for determining relative connections between individuals in accordance with some embodiments.

FIG. 1 is a functional diagram illustrating a programmed computer system for determining relative connections between individuals in accordance with some embodiments. As will be apparent, other computer system architectures and configurations can be used to determine relative connections. Computer system 100, which includes various subsystems as described below, includes at least one microprocessor subsystem (also referred to as a processor or a central processing unit (CPU)) 102. For example, processor 102 can be implemented by a single-chip processor or by multiple processors. In some embodiments, processor 102 is a general purpose digital processor that controls the operation of the computer system 100. Using instructions retrieved from memory 110, the processor 102 controls the reception and manipulation of input data, and the output and display of data on output devices (e.g., display 118). In some embodiments, processor 102 includes and/or is used to provide path finding functions described below with respect to FIGS. 4-11.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data, and objects used by the processor 102 to perform its functions (e.g., programmed instructions). For example, memory 110 can include any suitable computer-readable storage media, described below, depending on whether, for example, data access needs to be bi-directional or uni-directional. For example, processor 102 can also directly and very rapidly retrieve and store frequently needed data in a cache memory (not shown).

A removable mass storage device 112 provides additional data storage capacity for the computer system 100, and is coupled either bi-directionally (read/write) or uni-direction-ally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by the processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or tele-communications network using a network connection as shown. For example, through the network interface 116, the processor 102 can receive information (e.g., data objects or program instructions) from another network or output infor-mation to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process embodiments dis-closed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized inter-faces that allow the processor 102 to send and, more typically, receive data from other devices such as micro-phones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer read-able medium that includes program code for performing various computer-implemented operations. The computer-readable medium is any data storage device that can store data which can thereafter be read by a computer system. Examples of computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 1 is but an example of a computer system suitable for use with the various embodiments disclosed herein. Other computer systems suitable for such use can include additional or fewer sub-systems. In addition, bus 114 is illustrative of any intercon-nection scheme serving to link the subsystems. Other com-puter architectures having different configurations of subsystems can also be utilized.

Figure 2:
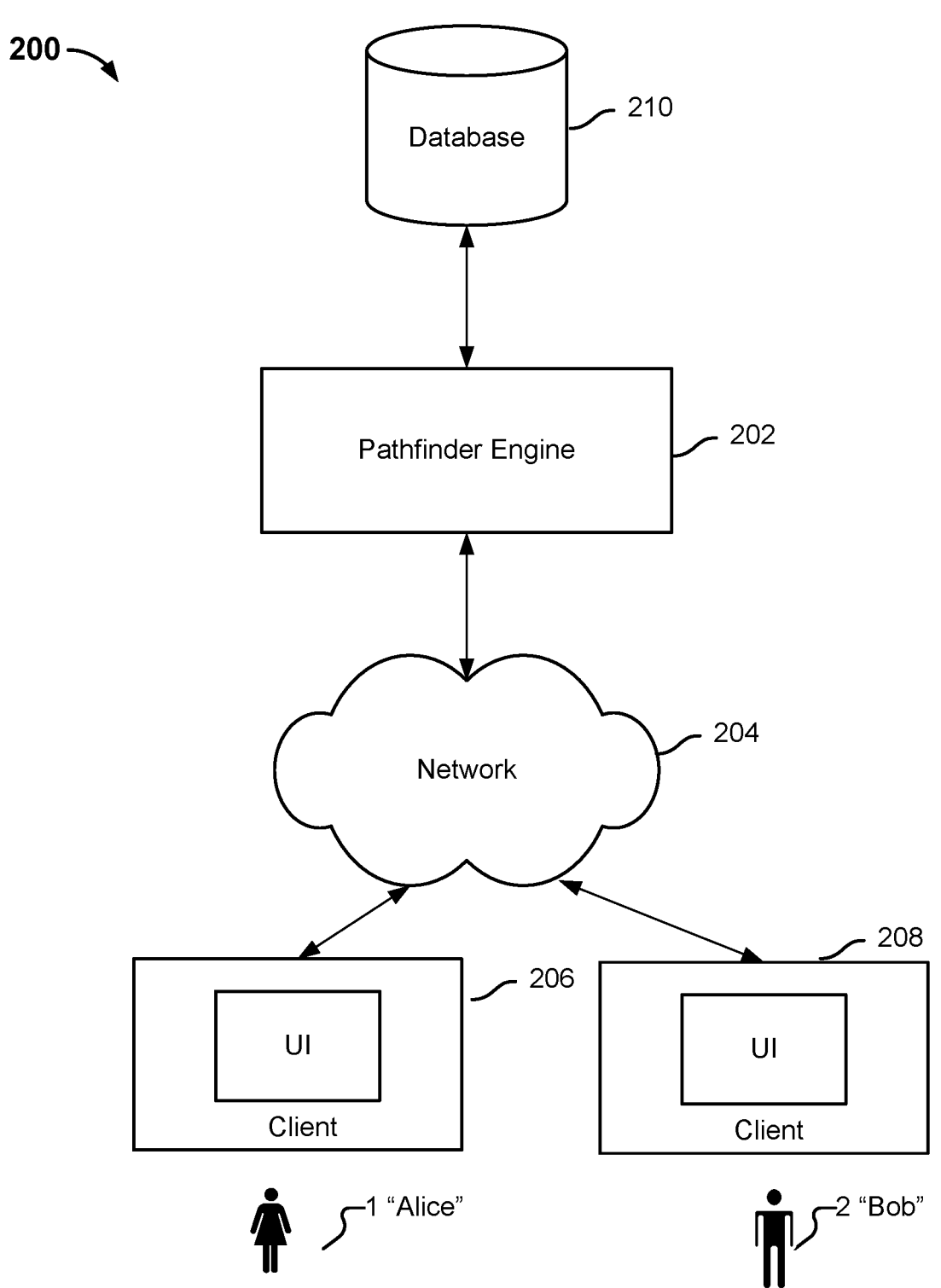
FIG. 2 is a block diagram illustrating an embodiment of a platform configured to determine relative connections between individuals.

FIG. 2 is a block diagram illustrating an embodiment of a platform configured to determine relative connections between individuals. In this example, relative connections path identification system 202 (also referred to as the pathfinder engine) may be implemented using one or more computers having one or more processors, one or more special purpose computing appliances, or any other appro-priate hardware, software, or combinations thereof. The operations of the imputation engine are described in greater detail below.

In this example, personal information (including genetic information, phenotype information, family information, population group information, etc., or a combination thereof) pertaining to a plurality of individuals is stored in a database 210, which can be implemented on an integral storage component of the imputation engine, an attached storage device, a separate storage device accessible by the imputation engine, or a combination thereof.

At least a portion of the database includes genotype data, specifically genotype data of genetic markers of individuals' deoxyribonucleic acid (DNA). Examples of such genetic markers include Single Nucleotide Polymorphisms (SNPs), which are points along the genome each corresponding to two or more common variations; Short Tandem Repeats (STRs), which are repeated patterns of two or more repeated nucleotide sequences adjacent to each other; and Copy-Number Variants (CNVs), which include longer sequences of DNA that could be present in varying numbers in different individuals. Although SNP-based genotype data is described extensively below for purposes of illustration, the technique is also applicable to other forms of genotype data such as STRs, CNVs, etc.

In this example, genotype data is used to represent the individuals' genomes. In some embodiments, the genotype data is obtained from DNA samples such as saliva or blood submitted by individuals. The genotype data can be obtained while an individual is still alive, or posthumously. The laboratory analyzes the samples using a genotyping platform, for example the Illumina OmniExpress™ genotyping chip, which includes probes to assay allele values for a specific set of SNPs. One genotyping process is known as hybridization, which yields different hybridization intensity values for each allele. The laboratory assigns genotype values to the alleles of each SNP by comparing the relative strength of these intensities. The resulting genotype data is stored in database 210. Other genotyping techniques can be used.

In some embodiments, the pathfinder engine is a part of a personal genomic services platform providing a variety of services such as genetic counseling, ancestry finding, social networking, etc. In some embodiments, individuals whose data is stored in database 210 are registered users of a personal genomic service platform, which provides access to the data and a variety of personal genetics-related services that the individuals have consented to participate in. Users such as Alice and Bob are genotyped and their genotype data is stored in database 210. They access the platform via a network 204 using client devices such as 206 and 208, and interact with the platform via appropriate user interfaces (UIs) and applications. For example, a pathfinder application implemented as a browser enabled application or a stand-alone application is used by the users to identify specific connection paths to other individuals in the database.

A relative connections graph is formed based on data in database 210 and used by the pathfinder engine. In various embodiments, the relative connections graph is formed based on genetic analysis of relative relationships, user-reported relative relationships, or a combination thereof. For purposes of example, the relative connections graph described in detail below is formed primarily based on genetically determined relative relationships, specifically relative relationships of individuals who are deemed to have descended from a common ancestor within a certain number (N) of generations. The technique is also applicable to other types of relative relationships such as relative relationships due to marriage, relative relationships determined using other means such as self-reporting by the individuals themselves, etc.

Figure 3:
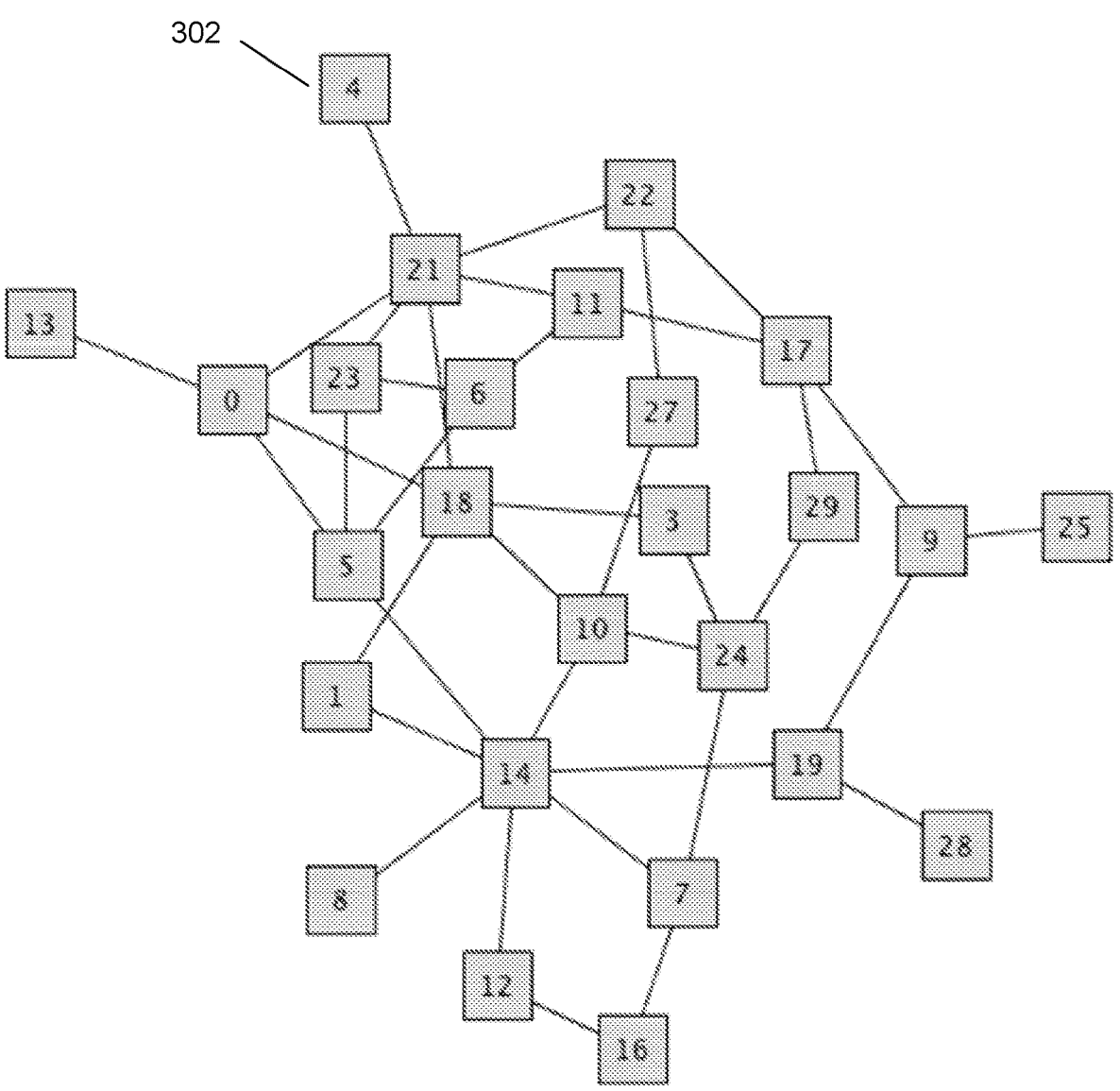
FIG. 3 is an example of a relative connections graph.

FIG. 3 is an example of a relative connections graph. In the diagram shown, a node such as 302 represents an individual, such as a user of a personal genomic services platform such as 200. A line connecting two individuals represents a family relationship, in particular a genetic relative relationship, between these two individuals. Two individuals have a genetic relative relationship if they are deemed to have descended from a common ancestor within a certain number of generations. For example, the individuals labeled 4 and 21 are cousins, both users of personal genomic services platform. The absence of a line connecting two individuals (e.g., individuals 4 and 13) indicates that, as far as the platform is aware, there is no genetic relative relationship between those two people. In other words, the individuals do not share a common ancestor within N generations.

In some embodiments, a relationship is assigned a weight, which is represented by the length of the line representing the relationship. A smaller weight indicates a closer relationship. For example, the relationship between individuals 10 and 24 is father and son, and the relationship between individuals 14 and 19 is third cousins. Accordingly, the line connecting 10 and 24 is shorter than the line connecting 14 and 19. Other representations of relationships are possible; for example, a greater weight may be used to indicate a closer relationship in some embodiments.

In some embodiments, the graph is available to be viewed by a user via a user interface display similar to FIG. 3. Although a visual representation is shown for purposes of illustration, in some embodiments it is sufficient to represent the individuals and their family relationships using data structures, and a display of the graph is not required.

The relative connections graph can be formed based at least in part on user-reported data. For example, via a family tree interface, user 1 reports that user 14 is her uncle and thus establishes the connection between them. In some embodiments, the relative connections graph is formed based at least in part on genetic data. For instance, 23andMe® provides a Relative Finder feature to automatically identify relative relationships on the basis of shared genetic material. Relatives are identified based on "Identity by Descent" (IBD) regions of their DNA. Because of recombination and independent assortment of chromosomes, the autosomal deoxyribonucleic acid (DNA) and X chromosome DNA (collectively referred to as recombinable DNA) from the parents is shuffled at the next generation, with small amounts of mutation. Thus, only relatives will share long stretches of genome regions where their recombinable DNA is completely or nearly identical. Such regions are referred to as IBD regions because they arose from the same DNA sequences in an earlier generation. IBD regions of two individuals' genomes or genotype sequences are determined using tools such as fastIBD™ or other appropriate techniques. Based on statistical distribution patterns of the amount of IBD shared and the degree of relationship (i.e., the number of generations within which two people share an ancestor), a predicted degree of relationship is determined. Additional details of how to determine relative relationships based on IBD regions are described in U.S. Pat. No. 8,463, 554 entitled FINDING RELATIVES IN A DATABASE which is incorporated herein by reference in its entirety for all purposes.

The relative connections graph is used by the pathfinder engine to identify the shortest path between two individuals. In various embodiments, the length of the path is measured by the number of connections, sum of weight associated with connections in the path, any other appropriate metrics, or combinations thereof. A user of the genomics services platform can invoke pathfinding for any individuals on the platform this user is permitted to see. For example, a first user invokes pathfinding to identify the relative relationships between him and a second user. The first user may find the second user by name or other types of search, select the second user from an extended family tree, or otherwise identify the second user.

Figure 4:
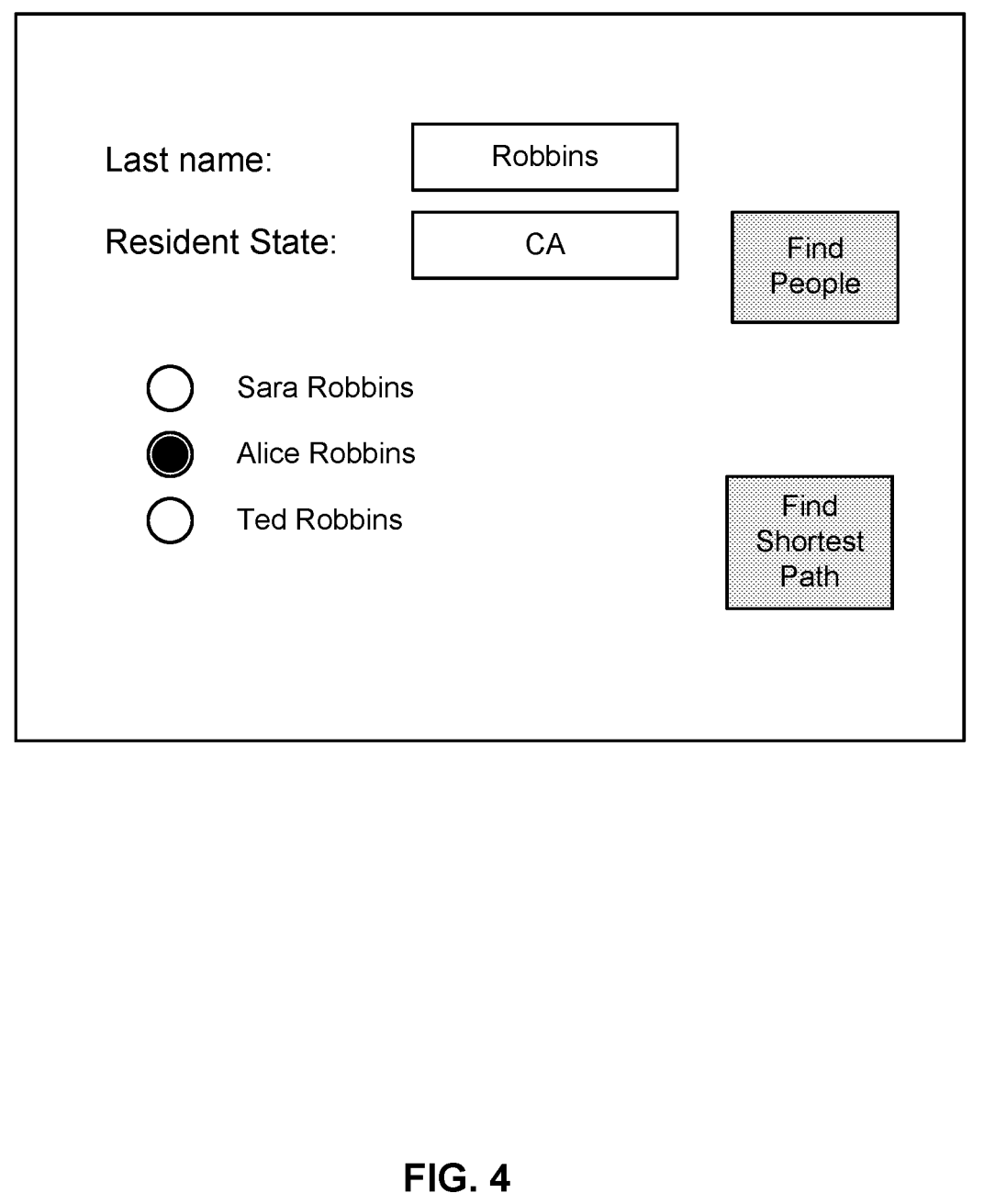

FIG. 4 is an example user interface used to invoke the pathfinding application. In this example, a user named Jerry Maxwell applies a number of filtering criteria (specifically, last name and resident state) to a search, and selects a user named Alice Robbins among the search results. Jerry then invokes the pathfinding application by clicking on the "find shortest path" button. FIG. 4 illustrates but one way of invoking the pathfinding application. There are many alternative ways of invocation, such as selecting a user from a family tree, a list of relatives, etc.

Figure 5:
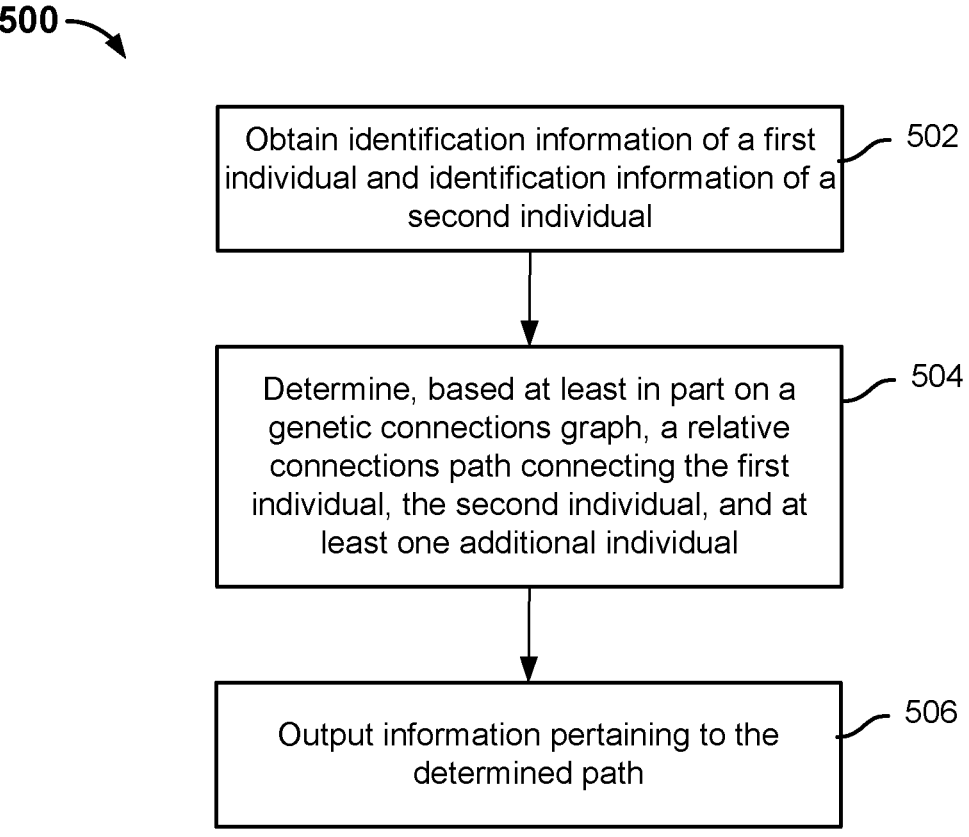
FIG. 5 is a flowchart illustrating an embodiment of a process of identifying the shortest path between two individuals.

FIG. 5 is a flowchart illustrating an embodiment of a process of identifying the shortest path between two individuals. Process 500 may be implemented on a system such as 100 or 202.

At 502, identification information of a first individual and identification information of a second individual are obtained. In some embodiments, the identification information is obtained as input parameters to the pathfinding function. In some embodiments, the identification information of at least one of the individuals is obtained by analyzing the context in which the process is invoked. For example, when Jerry Maxwell identifies Alice Robbins as one of the individuals involved in the pathfinding process, the context of the invocation identifies Jerry as another individual involved in the pathfinding process.

At 504, based at least in part on a genetic connections graph such as the one shown in FIG. 3, a specific genetic connections path is determined which connects the first individual, the second individual, and one or more additional related individuals.

In some embodiments, the specific connections path is the shortest path. The length of a path can be measured in different ways. In some embodiments, the length of a path is determined based on the number of connections in the path, and the shortest path corresponds to a path connecting two individuals with the fewest number of connections. Referring to FIG. 3 for an example, the shortest path between individuals 1 and 19 has two connections via individual 14. In some embodiments, the connections are associated with weights and a lesser weight represents a closer relationship; accordingly, the length of a path is determined based on a weighted sum of the connections, and the shortest path corresponds to a path having the least weighted sum. Referring again to FIG. 3, assume that the connection between individuals 14 and 12 has a weight of 4, and the connection between 12 and 16 has a weight of 2. The path between 14 and 16 via 12 has a length of 6. Also assume that the connection between 14 and 7 has a weight of 3, and the connection between 7 and 16 has a weight of 2. The path between 14 and 16 via 7 has a length of 5, which is shorter than the path between 14 and 16 via 12. In some embodiments, a combination of number of connections and weights is used to determine the shortest path; for example, the shortest path can be specified as a path with the least number of connections, and if multiple paths have the same number of least connections, the shortest path corresponds to the path with the least weighted sum of connections (thus a path with two connections will always be deemed to be shorter than a path with three connections regardless of the weight sums of the connections). In some embodiments, the measurement of the shortest path is configurable, and different ways of measuring the shortest path can be applied.

A number of techniques are usable to determine the specific genetic connections path. Two example techniques (breadth-first search and weighted Dijkstra) are described in greater detail below. Any other appropriate graph-based search techniques can be used.

At 506, information pertaining to the determined path is output. In some embodiments, the path is shown in a user interface display. Additional information about individuals included in the path, such as their profile or other metadata information, their relationships to each other, etc., is optionally output.

Figure 6:
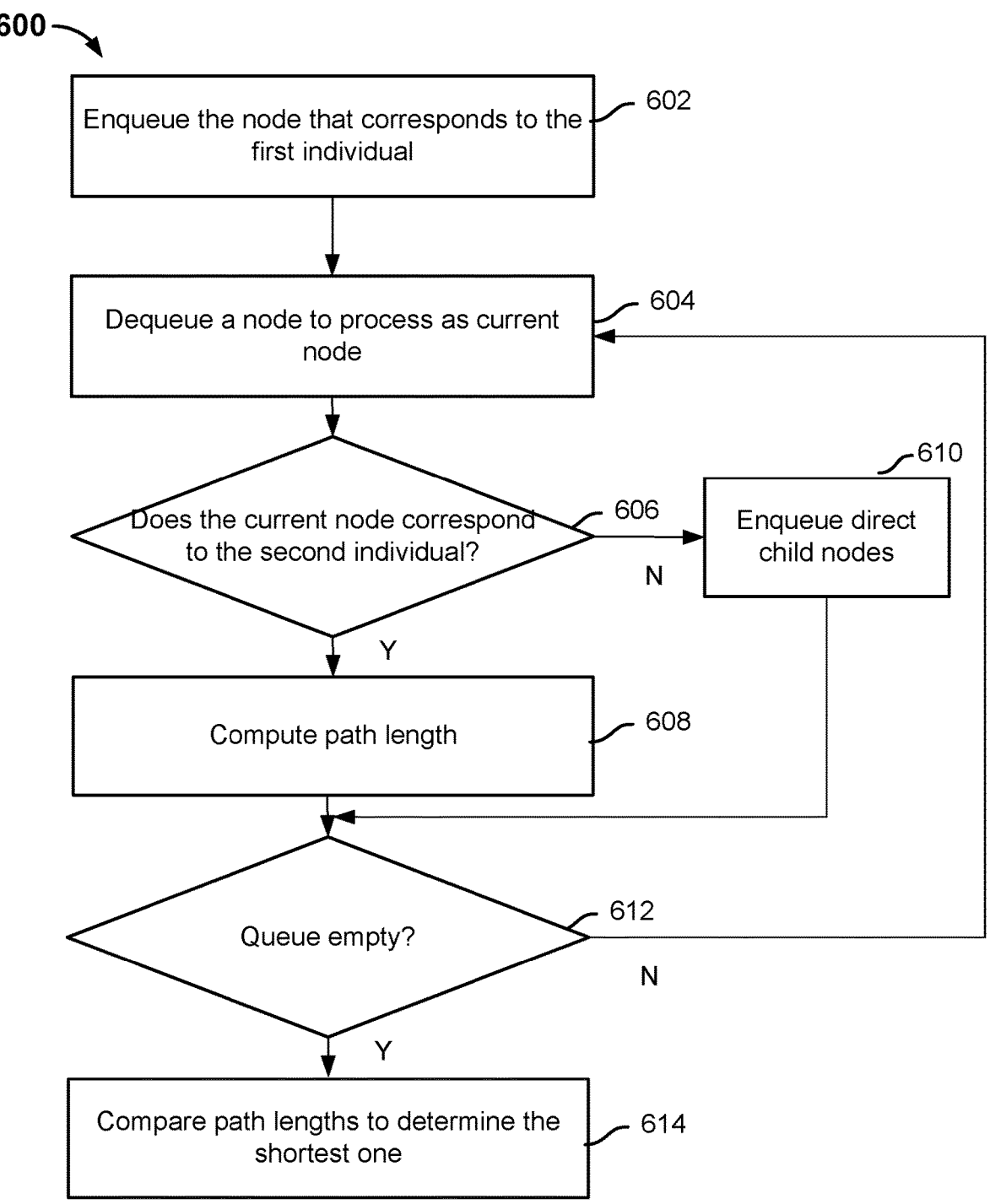
FIG. 6 is a flowchart illustrating an embodiment of a breadth first search process.

In some embodiments, breadth-first search is applied to the genetic connections graph to identify the shortest path. FIG. 6 is a flowchart illustrating an embodiment of a breadth first search process. Process 600 can be used to implement

504 of process 500. The process employs a queue data structure to store intermediate results as the graph is traversed.

At 602, the node corresponding to the first individual is enqueued (i.e., added to the queue).

At 604, a node is dequeued (i.e., removed from the queue). This node is also referred to as the current node.

At 606, it is determined whether the current node corresponds to the second individual. If so, a path is found and at 608, the length of the path connecting the first individual and the second individual is computed. Depending on implementation, the computation includes counting the number of connections, computing a weighted sum of the connections, or a combination. The result is kept on record (e.g., in memory or other storage) for later comparison.

If the current node does not correspond to the second individual, then, at 610, any direct child nodes (i.e., nodes connected to the current node) that have not yet been processed are enqueued.

At 612, it is determined whether the queue is empty.

If the queue is not empty, process returns to 604 to be repeated.

If the queue is empty, then every node on the graph has been examined. Process continues to 614, where the lengths of all the computed paths (e.g., results obtained from 608) are compared to determine the shortest path.

Figure 7:
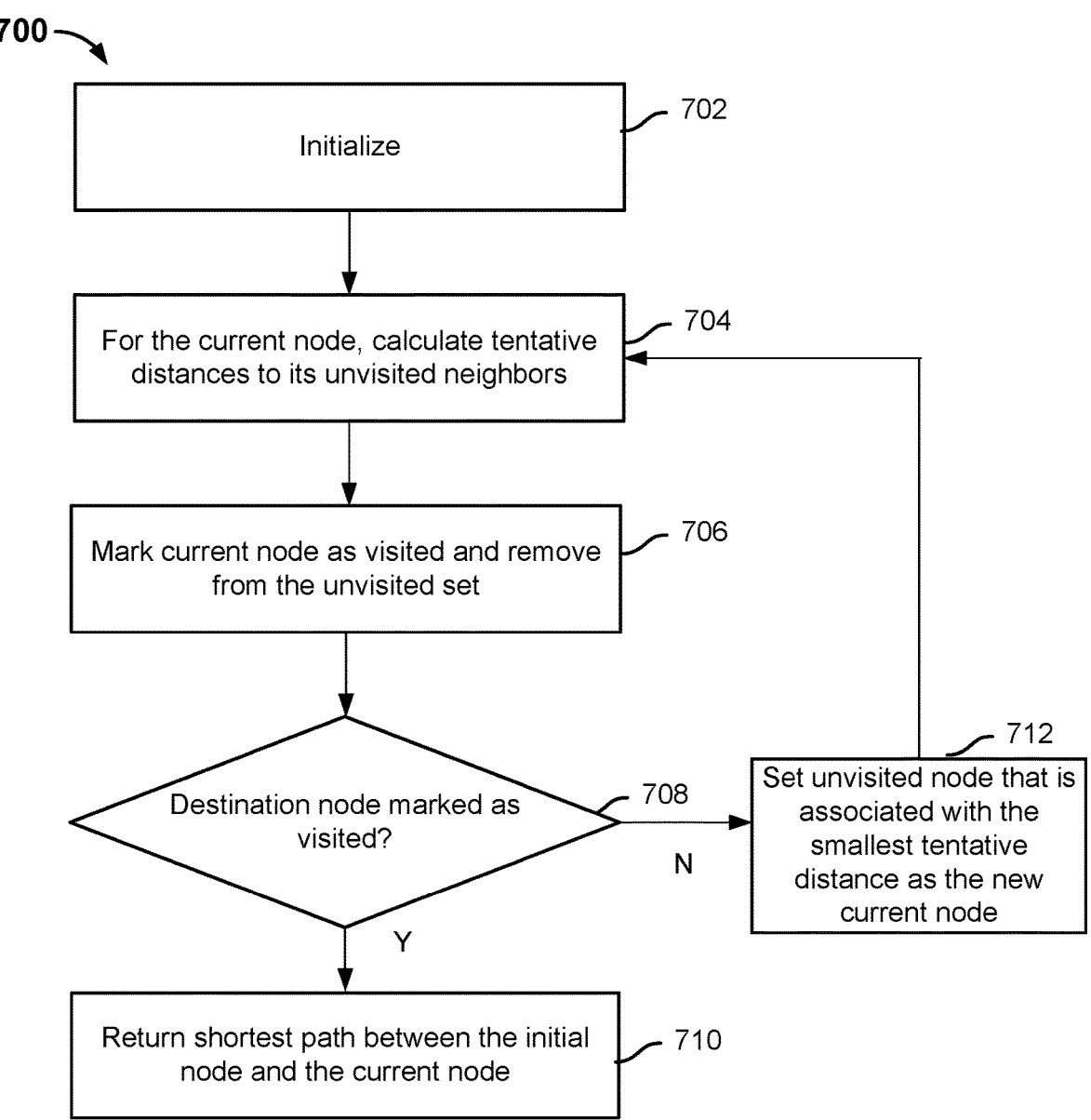
FIG. 7 is a flowchart illustrating an embodiment of a Dijkstra's Algorithm-based search process.

In some embodiments, Dijkstra's Algorithm is used to identify the shortest path on the genetic connections graph. FIG. 7 is a flowchart illustrating an embodiment of a Dijkstra's Algorithm-based search process. Process 700 can be used to implement 504 of process 500.

At 702, the process is initialized. Specifically, every node in the genetic connections graph is assigned a tentative distance value, 0 for the initial node corresponding to the first individual and infinity for all other nodes; all nodes are marked as unvisited; the initial node corresponding to the first individual is set as the current node; a set of the unvisited nodes forms an unvisited set, which comprises all of the nodes except the initial node.

At 704, for the current node, tentative distances to its unvisited neighbors are calculated and kept on record. For example, if the current node ("Bob Smith") has a tentative distance of 6, and the connection with a neighbor ("Clara Jones") has a weighted length of 2, then the distance to Clara Jones (through Bob Smith) will be 6+2=8. If this distance is less than the previously recorded tentative distance of Clara Jones (e.g., infinity), then the previous tentative distance is overwritten. At this point the neighbor nodes remain in the unvisited set.

At 706, the current node is marked as visited and is removed from the unvisited set.

At 708, it is determined whether the destination node (i.e., the node corresponding to the second individual) has been marked as visited. If so, at 710, the tentative distance associated with the destination node is deemed to be the shortest path and returned; otherwise, at 712, the unvisited node that is associated with the smallest tentative distance is set as the new current node, and the process returns to 704.

Breadth-first search and Dijkstra's Algorithm are example techniques used to identify the shortest path. Other techniques such as iterative deepening depth-first search can also be used.

Figure 8:
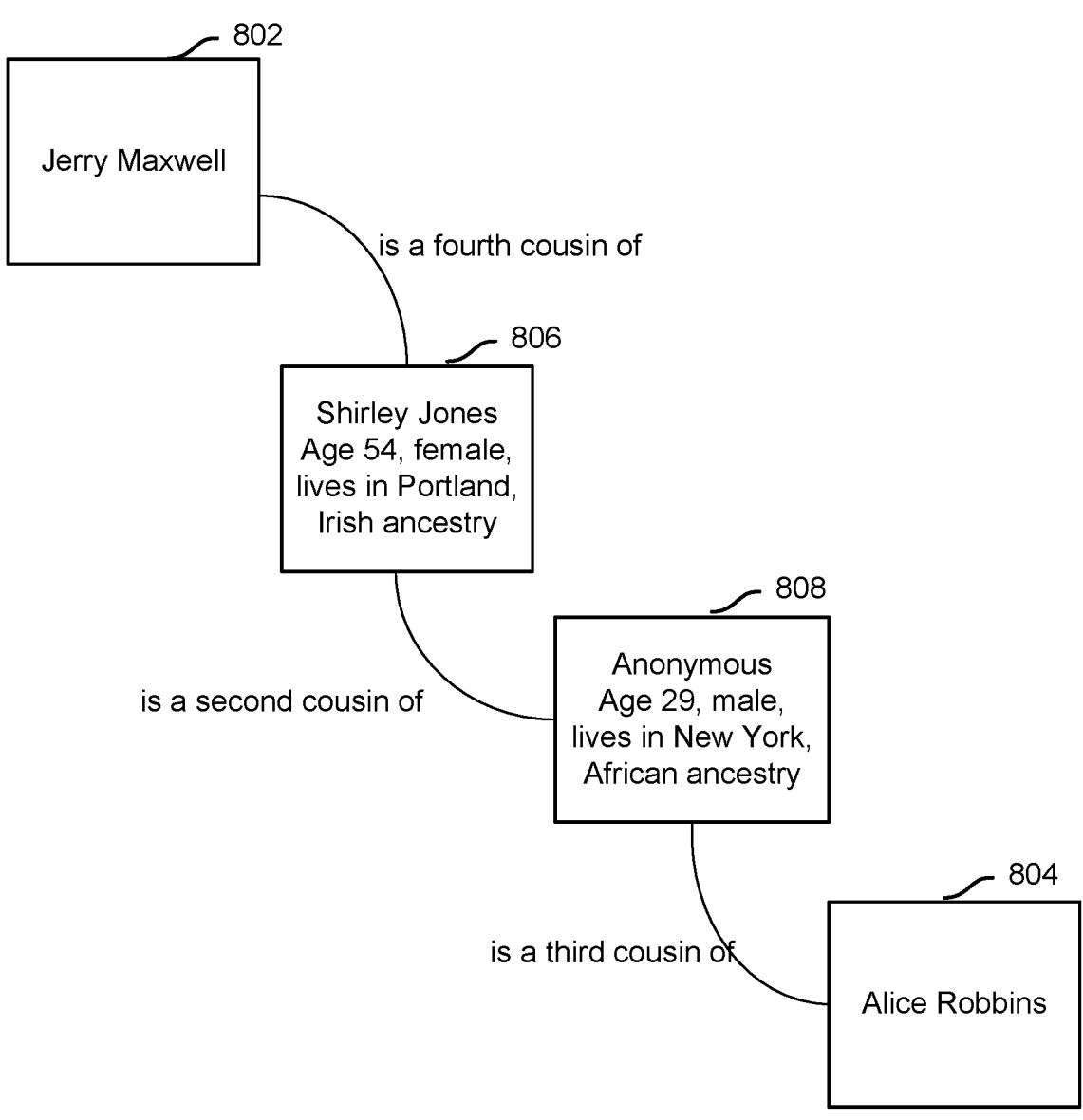
FIG. 8 is an example of a user interface displaying the result.

Once the shortest path is determined, the result is optionally displayed to the user who invoked the pathfinding function to inform the user of how the two focal individuals are connected. FIG. 8 is an example of a user interface displaying the result. In this example, each box represents a possibly-genotyped individual of the personal genomic services platform. Boxes 802 and 804 represent individuals Jerry Maxwell and Alice Robbins, respectively, who are the "focal" pair of individuals between whom a relative connections path is found. Boxes 806 and 808 represent individuals who are relatives of the focal pair individuals as indicated. For example, Jerry Maxwell and Shirley Jones are individuals whose genotype data is made available to the personal genomics services platform. Based on an IBD-based relative finding technique described above, the system identifies Jerry and Shirley as related, with an estimated relationship of fourth cousin. The path between Jerry and Alice includes Shirley and an anonymous individual identified as a second cousin of Shirley Jones and a third cousin of Alice Robbins. The identities of the individuals associated with the path, if known, are displayed. Their respective connections and relationships are also displayed.

In this example, Shirley Jones has authorized the platform to display her name in the pathfinding application. The individual represented by box 808, however, has not given authorization to display his name, and is therefore shown as "Anonymous." Both Shirley and Anonymous have authorized certain metadata to be displayed. In this example, the metadata includes certain profile information provided by Shirley and Anonymous such as age, gender, and current city of residence. The metadata displayed can also include certain information inferred by the system. For example, by comparing the individuals' genotype information (e.g., DNA markers) with reference individuals known to be of a specific ancestry, it is determined that Shirley is of Irish ancestry and Anonymous is of African ancestry.

In some embodiments, the pathfinder application permits a user to select a celebrity as an individual in a focal pair. For example, instead of Alice Robbins, the second individual may be specified as Sergey Brin or Albert Einstein. How celebrities are identified depends on implementation. In some embodiments, a system administrator manually identifies celebrities as they join the personal genomics services platform, and marks their personal data accordingly. In some embodiments, celebrities are automatically identified by comparing their names and occupation with a database of celebrities. In some embodiments, out of privacy concerns, the platform places certain restrictions on how connections near a celebrity may be displayed. For example, paths including close relatives (e.g., people who are relatives within two generations) are excluded from consideration in some embodiments; as another example, in some embodiments, on a path involving a close relative of a celebrity, the name and metadata associated with that close relative are not displayed.

Figure 9:
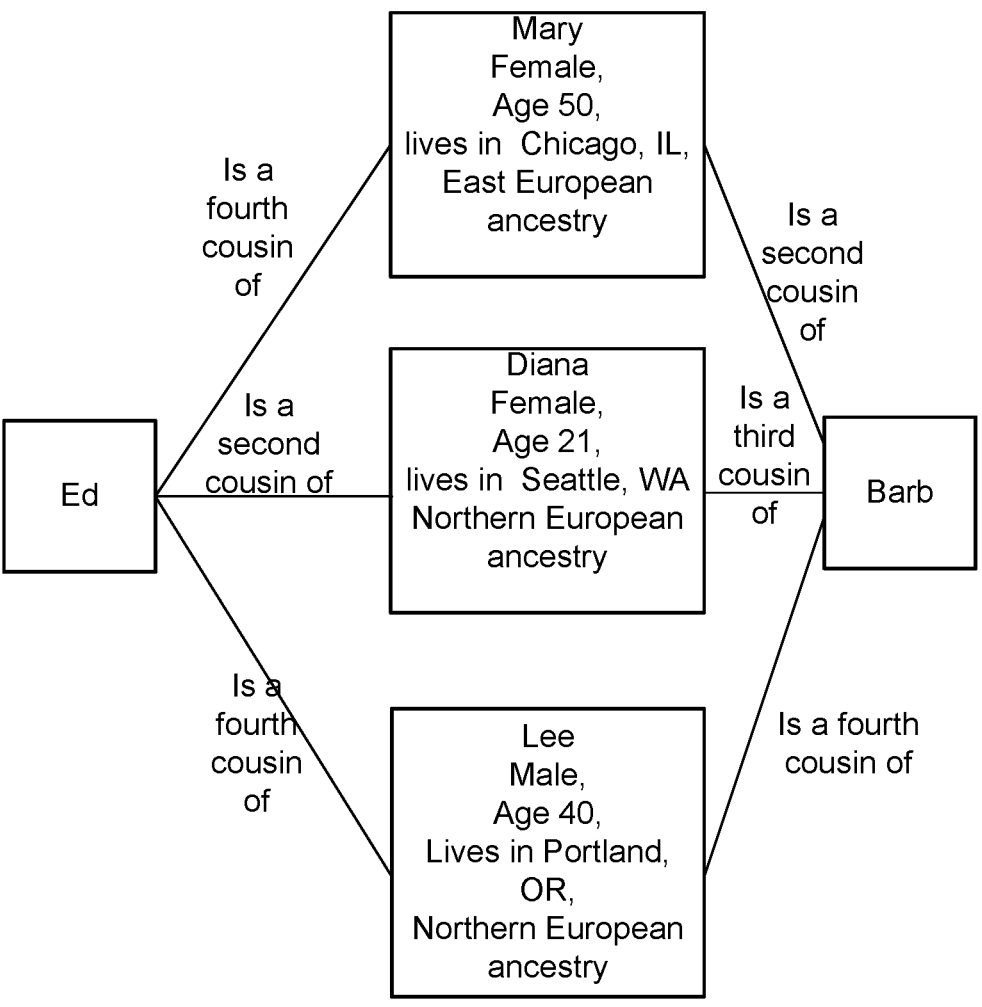
FIG. 9 is a diagram illustrating an example in which multiple shortest paths are displayed.

In some cases, multiple shortest paths are found. FIG. 9 is a diagram illustrating an example in which multiple shortest paths are displayed. In this example, the length of a path equals the number of connections in the path. Thus, for the focal pair of individuals Ed and Barb, there are three paths of length two, passing through Mary, Diana, and Lee, respectively.

Figure 10:
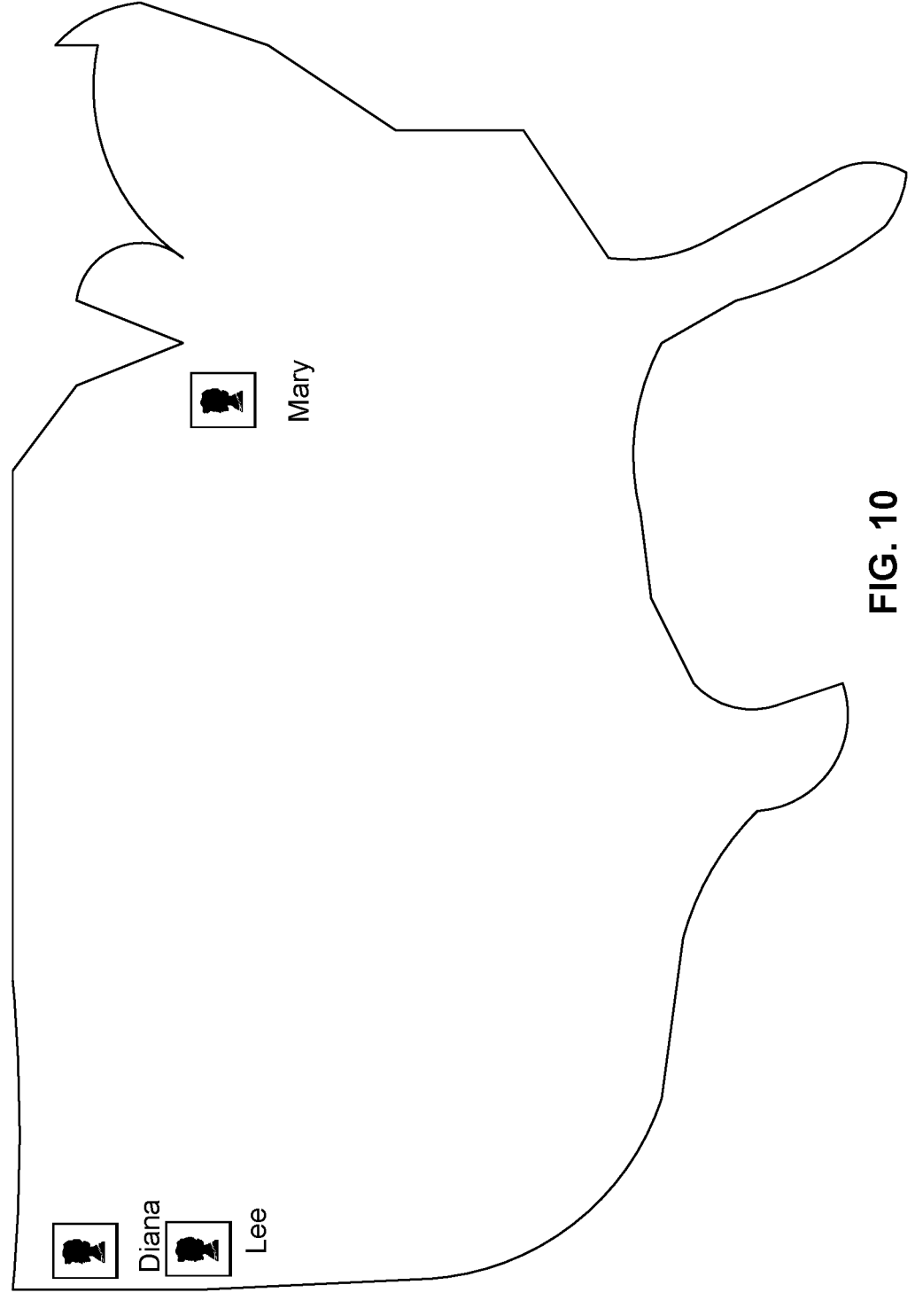
FIGS. 10 and 11 are example user interface displays of aggregated metadata for multiple shortest paths.
Figure 11:
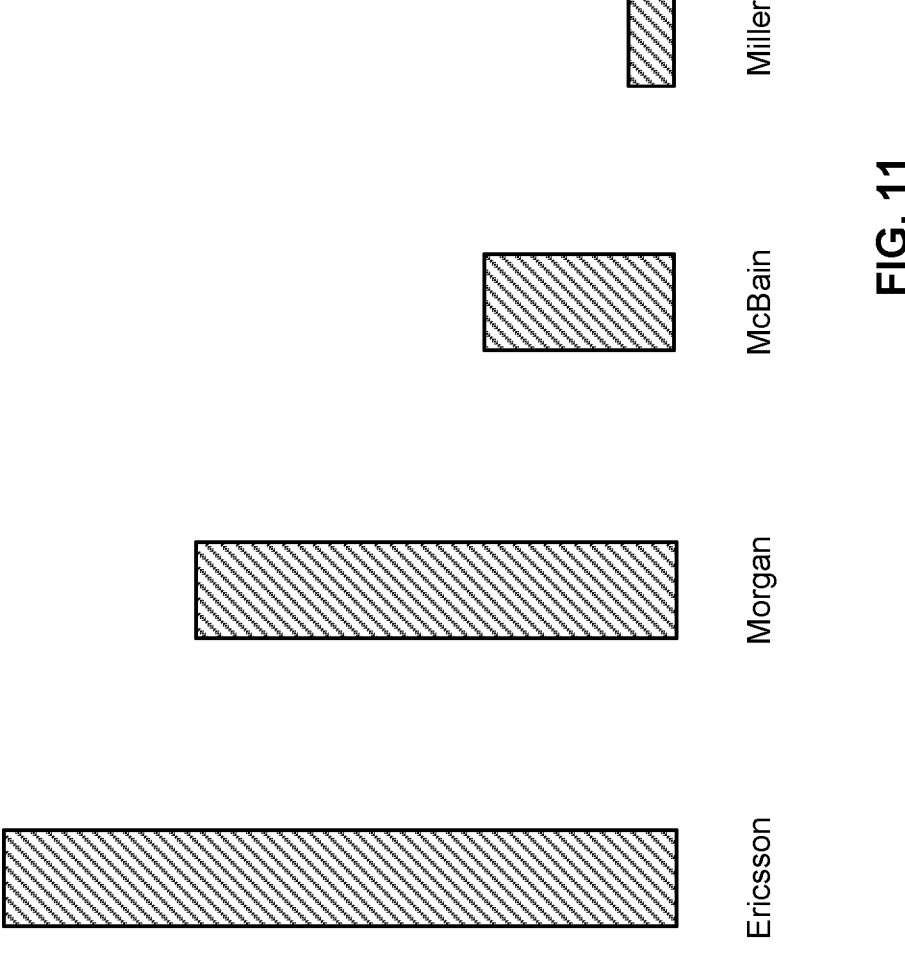

In some embodiments, instead of or in addition to displaying metadata of the individuals in the paths in the manner shown in FIG. 9, the metadata is displayed in aggregate. FIGS. 10 and 11 are example user interface displays of aggregated metadata for multiple shortest paths. In FIG. 10, geographical locations associated with the intermediate individuals are displayed on a map, giving the viewer a sense of where these relatives reside and potentially how the family may have migrated over time. In FIG. 11, aggregated surnames associated with the intermediate individuals are displayed. Specifically, the surnames of the intermediate individuals (and optionally the surnames of their relatives within a preset number of generations) are tallied and displayed in a histogram of surnames to give the viewer a clearer picture of how the individuals are related to the focal pair. In the example shown, among Mary, Diana, and Lee and their relatives, the dominant surnames are Ericsson, Morgan, McBain, and Miller. If the histogram is dominated by surnames that appear frequently in Ed's maternal side of the family, then Barb is likely a relative on the maternal branch of the family.

Finding a relative connection path between two individuals in a database has been described. By utilizing a relative connections graph, the pathfinder application can quickly determine a shortest connection path, providing insight into how the individuals are related.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of presenting, to a user of a personal genomic services platform, information related to relative connections between a first focal individual and a second focal individual who do not share a common ancestor within a threshold number of generations, the method comprising:

receiving, from the user, a request to invoke pathfinding between the first focal individual and the second focal individual, wherein pathfinding comprises identifying a set of relative connections that connects the first focal individual to the second focal individual through one or more intermediate individuals, wherein the user has permission within the personal genomics services platform to see the first focal individual and the second focal individual, and wherein the request comprises:
    a selection of the second focal individual by name;
    a selection of the second focal individual from an extended family tree; or
    a selection of the second focal individual from a list of relatives;

forming, using one or more computer processors, a relative connections data structure that indirectly connects the first focal individual to the second focal individual through one or more intermediate individuals, wherein at least one of the intermediate individuals is directly connected to the first focal individual, wherein at least one of the intermediate individuals is directly connected to the second focal individual, wherein each direct connection between two individuals in the relative connections data structure indicates that, as far as the personal genomic services platform has determined, the two individuals share a common ancestor within the threshold number of generations, and wherein an absence of a direct connection between two individuals in the relative connections data structure indicates that, as far as the personal genomic services platform has determined, the two individuals do not share a common ancestor within the threshold number of generations; and displaying, to the user, information pertaining to the relative connections data structure, wherein the information displayed to the user comprises information related to the relative connections between the first focal individual and the second focal individual.

2. The method of claim 1, wherein the user is the first focal individual, wherein the method further comprises identifying, by the one or more processors, that the user is the first focal individual based on a context of the request to invoke pathfinding, and wherein the context of the request to invoke pathfinding comprises the request to invoke pathfinding being received from the user.

3. The method of claim 1, further comprising obtaining, from a database, genotype data of the first focal individual, the second focal individual, and the one or more intermediate individuals, wherein the relative connections data structure is formed at least in part based on the genotype data obtained from the database.

4. The method of claim 3, wherein each direct connection between two individuals in the relative connections data structure indicates that the two individuals are genetic relatives who share a common ancestor within the threshold number of generations as determined based on one or more Identical by Descent (IBD) regions shared between the two individuals.

5. The method of claim 1, further comprising obtaining, from a database, relative relationships reported by users of the personal genomic services platform, wherein the relative connections data structure is formed at least in part based on the relative relationships reported by users.

6. The method of claim 1, further comprising obtaining, from a database, relative relationships due to marriage, wherein the relative connections data structure is formed at least in part based on the relative relationships due to marriage.

7. The method of claim 1, wherein the information displayed to the user comprises age information, surname information, residence information, or ancestry information associated with at least one of the intermediate individuals.

8. The method of claim 7, wherein the information displayed to the user comprises:

information for which the intermediate individuals have provided authorization to display; or ancestry information associated with at least one of the intermediate individuals, wherein the ancestry information was inferred by the personal genomic services platform.

9. The method of claim 7, wherein displaying information pertaining to the relative connections data structure comprises displaying geographical locations associated with at least one of the intermediate individuals on a map or surname information in a histogram.

10. The method of claim 1, further comprising determining, based on the relative connections data structure, a shortest genetic connection between the first focal individual and the second focal individual.

11. The method of claim 10, wherein the shortest genetic connection between the first focal individual and the second focal individual is determined using a configurable measurement technique.

12. The method of claim 10, wherein each direct connection between two individuals in the relative connections data structure is assigned a weight based on the number of generations between the common ancestor and each of the two individuals, and wherein the shortest genetic connection between the first focal individual and the second focal individual is determined using the weights associated with each direct connection between the first focal individual and the second focal individual.

13. The method of claim 12, wherein the shortest genetic connection between the first focal individual and the second focal individual is determined using a least weighted sum of connections.

14. The method of claim 12, wherein the relative connections data structure comprises a graph, wherein a line represents a direct connection within the graph, and wherein a length of the line represents the weight based on the number of generations between the common ancestor and each of the two individuals.

15. The method of claim 10, wherein the shortest genetic connection between the first focal individual and the second focal individual is determined based on a minimum number of direct connections required to connect the first focal individual and the second focal individual.

16. The method of claim 1, wherein the request comprises the selection of the second focal individual by name.

17. The method of claim 1, wherein the request comprises the selection of the second focal individual from the extended family tree.

18. The method of claim 1, wherein the request comprises the selection of the second focal individual from the list of relatives.

19. A system for presenting, to a user of a personal genomic services platform, information related to relative connections between a first focal individual and a second focal individual who do not share a common ancestor within a threshold number of generations, the system comprising:

one or more processors configured to:

receive, from the user, a request to invoke pathfinding between the first focal individual and the second focal individual, wherein pathfinding comprises identifying a set of relative connections that connects the first focal individual to the second focal individual through one or more intermediate individuals, wherein the user has permission within the personal genomics services platform to see the first focal individual and the second focal individual, and wherein the request comprises:

a selection of the second focal individual by name;

a selection of the second focal individual from an extended family tree; or a selection of the second focal individual from a list of relatives;

form, a relative connections data structure that indirectly connects the first focal individual to the second focal individual through one or more intermediate individuals, wherein at least one of the intermediate individuals is directly connected to the first focal individual, wherein at least one of the intermediate individuals is directly connected to the second focal individual, wherein each direct connection between two individuals in the relative connections data structure indicates that, as far as the personal genomic services platform has determined, the two individuals share a common ancestor within the threshold number of generations, and wherein an absence of a direct connection between two individuals in the relative connections data structure indicates that, as far as the personal genomic services platform has determined, the two individuals do not share a common ancestor within the threshold number of generations; and display, to the user, information pertaining to the relative connections data structure, wherein the information displayed to the user comprises information related to the relative connections between the first focal individual and the second focal individual.

20. A computer program product for presenting, to a user of a personal genomic services platform, information related to relative connections between a first focal individual and a second focal individual who do not share a common ancestor within a threshold number of generations, the computer program product being embodied in a non-transitory computer readable storage medium and comprising computer instructions for:

receiving, from the user, a request to invoke pathfinding between the first focal individual and the second focal individual, wherein pathfinding comprises identifying a set of relative connections that connects the first focal individual to the second focal individual through one or more intermediate individuals, wherein the user has permission within the personal genomics services platform to see the first focal individual and the second focal individual, and wherein the request comprises:

a selection of the second focal individual by name;

a selection of the second focal individual from an extended family tree; or a selection of the second focal individual from a list of relatives;

forming, a relative connections data structure that indirectly connects the first focal individual to the second focal individual through one or more intermediate individuals, wherein at least one of the intermediate individuals is directly connected to the first focal individual, wherein at least one of the intermediate individuals is directly connected to the second focal individual, wherein each direct connection between two individuals in the relative connections data structure indicates that, as far as the personal genomic services platform has determined, the two individuals share a common ancestor within the threshold number of generations, and wherein an absence of a direct connection between two individuals in the relative connections data structure indicates that, as far as the personal genomic services platform has determined, the two individuals do not share a common ancestor within the threshold number of generations; and displaying, to the user, information pertaining to the relative connections data structure, wherein the information displayed to the user comprises information related to the relative connections between the first focal individual and the second focal individual.

* * * * *